United States Patent [19]

Britt et al.

[11] Patent Number: 5,462,868
[45] Date of Patent: Oct. 31, 1995

[54] COCAINE ESTERASE FROM PSEUDOMONAS SP. NCIMB 40427 FOR DETECTION OF COCAINE

[75] Inventors: Adrian J. Britt, Culcheth; Neil C. Bruce, Cambridge; Christopher R. Lowe, Saffron Walden, all of England

[73] Assignee: British Technology Group Limited, London, England

[21] Appl. No.: 185,835

[22] PCT Filed: Jul. 20, 1992

[86] PCT No.: PCT/GB92/01324

§ 371 Date: Jan. 26, 1994

§ 102(e) Date: Jan. 26, 1994

[87] PCT Pub. No.: WO93/02186

PCT Pub. Date: Feb. 4, 1993

[30] Foreign Application Priority Data

Jul. 22, 1991 [GB] United Kingdom ................ 9115765

[51] Int. Cl.$^6$ .................... C12N 9/16; C12N 1/20; C12Q 1/44
[52] U.S. Cl. ............... 435/196; 435/253.3; 435/874; 435/19
[58] Field of Search ................ 435/196, 253.3, 435/874, 19

[56] References Cited

FOREIGN PATENT DOCUMENTS

WO90/13634  11/1990  WIPO.

OTHER PUBLICATIONS van Zuthphen, Genen. Phaenen, 18(2–3): 83–86, 1975.
van Zutphen, Biochem. Genetics, 12(4), 1974, 327–343.
van Zutphen, Biochem. Genetics, 12(4), 1974, 309–326.
Brzezinski et al., Fed. Am. Soc. Exp. Biol., 7(7), 1993.
Landry et al., Science, 259, 1993, 1899–1901.
Ammon et al., Enzymol. ACTA. Biocat., v. 36(4–5), 239–48, 1969.
van Zutphen, Enzymologia, 42(3), 1972, 201–18.
C. Stormont and Y. Suzuki, "Atropinesterase and Cocainesterase of Rabbit Serum . . . " Science, 167, 200–202, (1970).
C. Araoz and C. Angel, "Plasma tropacocaine esterase activity . . . ", Clinical Chemistry, 22, 1203 (1976).
L. F. M. van Zutphen, M. G. C. W. den Bieman and J. Bouw, "Serum esterase genetics in rabbits. IV. Two additional systems.", Animal Blood Groups and Biochemical Genetics, 8, (Suppl. 1), 29–30, (1977).
C. Stormont and Y. Suzuki, "The atropinesterase-cocainesterase system of isozymes in rabbits . . . ", in Isozymes IV. Genetics and Evolution. 3rd International Conference, New Haven, Conn., USA, April 18–20, 1974, ed. C. L. Markert, Academic Press, N.Y. and London (1975), pp. 699–712.
Dean et al, "Cocaine metabolism . . . " FASEB Journal, vol. 5, No. 5, 3 Mar. 1991, Bethesda, Md., USA p. A1205.
Dean et al, "Human liver cocaine . . . " FASEB Journal, vol. 5, No. 12, Sep. 1991, Bethesda, Md., USA, pp. 2735–2739.
Britt et al., "Identification of a cocaine . . . ", Journal of Bacteriology, vol. 174, No. 7, 1992, pp. 2087–2094.
Cauthen et al., "Resolution, purification and characterization of rabbit serum atropinesterase and cocainesterase", Biochem. Pharmacol. 25, 181–185 (1976).

*Primary Examiner*—David M. Naff
*Assistant Examiner*—Mike Meller
*Attorney, Agent, or Firm*—Nixon & Vanderhye

[57] ABSTRACT

A cocaine esterase has been isolated from a strain of the bacteria *Pseudomonas maltophilta*. The cocaine esterase catalyses the debenzoylation of cocaine, This reaction may be used in the detection of cocaine. The enzyme may be incorporated into sensors for this purpose. The cocaine esterase is preferably obtainable from Pseudomonas sp. NCIMB 40427. It catalyzes the debenzoylation of cocaine, has a molecular weight in the unaggregated form of about 120,000 daltons as determined by gel filtration, has esterase activity specifically at the benzoate ester linkage of cocaine, separates at a major band of Rf about 0.2 on PAGE in its aggregated form, and it is completely inhibited by 1 mM phenylmethylsulphonyl fluoride but ineffectively inhibited by 1 mM eserine, each determined at 30° C. with respect to 2 mM cocaine as substrate.

5 Claims, 2 Drawing Sheets

COCAINE ESTERASE FROM PSEUDOMONAS SP. NCIMB 40427 FOR DETECTION OF COCAINE

BACKGROUND OF THE INVENTION

This invention relates to a new enzyme isolated from a microorganism, the microorganism that produces this enzyme, the use of this enzyme in catalysing the degradation of cocaine and a method and apparatus for the detection of cocaine using this enzyme.

DESCRIPTION OF THE PRIOR ART

There is an urgent need for a better method of detection of cocaine in particulate form and in body fluids. In relation to particulate cocaine, although many different analytical systems have been proposed, most are based on large pieces of equipment such as mass spectrometry, and require specially trained laboratory technicians. Such systems include thin layer chromatography, gas chromatography and high pressure liquid chromatography (HPLC). In relation to body fluids they require extraction of the sample to remove interfering compounds. Labelled assays have been used but these also require specialist skills to carry out. Some of the above or other prior methods, e.g. mass spectrometry, also require bulky and expensive equipment.

Portable detecting devices for cocaine have recently been developed. Thus, Einceman et al. (Anal. Chem. (1990) 62 1374–1379) have developed a portable ion mobility spectrometer, but it relies heavily on the volatility of the drug. A similar drawback exists with the piezoelectric crystal coated detecting device of Ngeh-Ngwainbi et al. (Biosensors & Biomechanics (1990) 5 13–26). A potentiometric sensor has been developed by K. Vytras et al., (Mikrochlmica Acta (1984) [Wein] III 139–148) but this is very unspecific as it forms a complex with the tertiary amine group present in many illicit drugs.

SUMMARY OF THE INVENTION

We have now found an enzyme which can be used in the detection of cocaine. The enzyme is a cocaine esterase (hereinafter CE) which catalyses the debenzoylation of cocaine that is to say its hydrolysis to produce ecgonine methyl ester and benzoic acid. This enzyme could thus be used to detect cocaine, by reacting the enzyme with cocaine and detecting the occurrence of the enzyme-catalysed reaction. One such method of detection would be conductimetric, as the CE reaction will bring about a change in conductance of the solution. Alternatively, the method of detection could be potentiometric, the CE reaction bringing about a change in the pH of the solution. Other methods could include optical, color,metric, thermometric or amperometric detection of the reaction products, such methods being well known in the art. Accordingly the Invention includes sensors, especially of the conductrimetric or potentiometric type for cocaine esterase. These and similar sensors can be used as the basis for convenient portable sensors for detecting cocaine in body fluids, luggage, clothing etc. of smugglers, traffickers and cocaine users. Accordingly the invention provides an important advance in the fight against and control of use of drugs.

The term "cocaine" used throughout the specification comprises the free base and salts thereof, unless the context requires a more specific meaning.

In a first aspect the invention provides the cocaine esterase enzyme. The cocaine esterase enzyme catalyses the debenzoylation of cocaine into ecgonine methyl ester and benzoic acid; thus it attacks the benzoate ester linkage of cocaine. There is little or no activity at the methyl ester linkage. Thus, ability to specifically attack the benzoate ester linkage of cocaine is a distinctive feature of the cocaine esterase of the invention, that is not possessed by commercially available esterases, e.g. porcine liver esterase, horse serum butyryl-cholinesterase or other esterases such as microbial atropinesterase.

Another distinctive feature of the CE is that it has a native molecular weight in its unaggregated form of about 120,000 Daltons and when aggregated of about 420,000 Daltons (both as determined by elution from a gel filtration column calibrated with protein markers). By the term "about" we mean to encompass variations which are usual in the determination of high molecular weights by this method and certainly to include a variation of up to 10%. This molecular weight is considerably different from that of microbial atropinesterase which has a molecular weight of 30,000 Daltons when denatured and 60,000 Daltons in its native form (Rorsch et al., Proc. K. Ned. Akad. Wet. (1971) Set. C 74 132–152).

Example 3 hereinafter describes other features of the CE, but it is expected that it will be possible to vary some of these by changing the conditions of growth of the microorganism which produces it, or by a higher degree of purification of the enzyme. Accordingly, it is not preferred to rely on such characteristics as the catalytic activity or the thermal stability of CE in the most general definition of the enzyme. Any one, or more of them can be permitted (as the context permits) as alternative ways of defining the enzyme, but they are best seen as one or more preferred, additional characteristics to one or more of those defined above.

The CE is obtained from a bacterial strain isolated from nature. The bacterial strain is a strain of *Pseudomonas maltophilia* herein designated "MB11L". A Budapest Treaty patent deposit of this bacterium has been made at the National Collections of Industrial and Marine Bacteria (NCIMB), 23 St. Machat Drive, Aberdeen, AB2 1RY, Scotland on the 14th June 1991 under the deposit number NCIMB 40427 and all restrictions on NCIMB 40427 will be irrevocably removed upon the issuance of a patent. Considerable difficulty lies in the exact taxonomical classification of some members of *Pseudomonas maltophilia* as they could equally be classified as *Xanthomonas maltophilia*. Pseudomonas has been preferred in this instance but this organism may also be classified within the genus Xanthomonas. This bacterium, together with mutants and variants producing the CE of the invention, are included in the present invention. The CE can be produced by culturing such a bacterium on a source of carbon and nitrogen.

DESCRIPTION OF THE PREFERRED EMBODIMENTS

Figure 1:
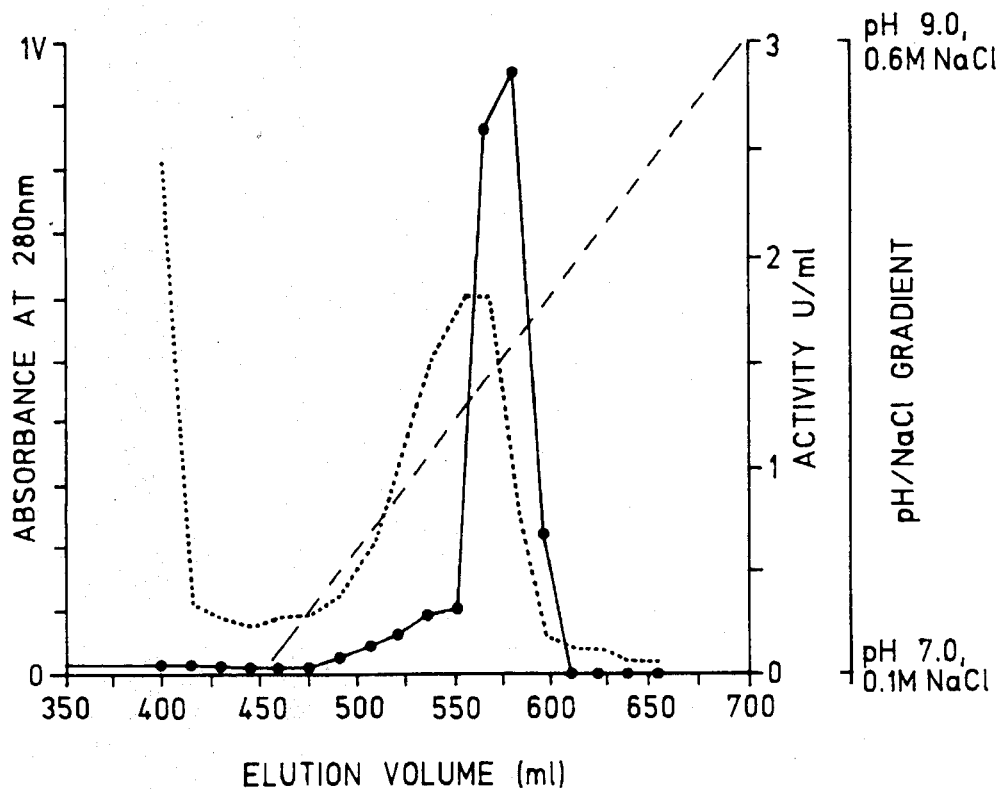
FIGS. 1 to 4 plot the course of important stages in the chromatographic purification of the CE (see Example 2).

Cocaine esterase can be produced by culturing *P. Maltophilia* on a source of carbon and nitrogen. Preferably the source is cocaine itself. When grown on glucose or benzoate the activity of the CE is lower than when grown on cocaine. Additionally D,L-methionine is preferably added to the growth medium as this increases the specific activity of the cocaine esterase produced. In an alternative, an equimolar mixture of cocaine and glucose yields an enzyme of high activity. Cultivation is preferably aerobic at any usual temperature, e.g. within 20° to 40° C. range, preferably 25° to 35° C. To obtain the enzyme the cells can be disrupted in any conventional way. Preferably a cell-free extract is made. The enzyme is then recovered from the cells or the extract.

Instead of the precise starting organism deposited, a mutant thereof, e.g. derived by gamma-ray irradiation or use of a chemical mutant, induction by culture on another medium etc. or a transconjugant thereof with another bacterium or an artificially produced variant can be used.

The enzyme or some modification thereof can also be made by recombinant DNA technology using methods well recognised in that art. These may entail producing the enzyme in another host organism.

The invention is particularly applicable to the detection of grains of powdered cocaine (free base or any of its salts) in luggage, cargo, or about the person, or for the detection of cocaine or its metabolites in biological fluids especially in urine and blood.

The enzyme of the present invention is of use primarily in the detection of cocaine. This may be achieved by the use of cocaine esterase enzyme alone or in conjunction with one or more other enzymes that will further improve the detection of cocaine.

The methods of making biosensors that rely on conductimetric, amperometric or potentiometric changes in the test reaction are well known in the art. UK Patent Application Publication No. 2,231,332A (NRDC) describes such methods and their use in biosensors, the contents of which in relation thereto is hereby Incorporated by reference.

Any of such methods may be of use in detecting the occurrence of the cocaine esterase reaction and hence in the detection of cocaine.

The cocaine esterase of the Invention has several other uses. It can be used to "clear" the body of excess cocaine after a cocaine overdose. Similarly the organism MB11L can be used to "clear" industrial waste of cocaine. The term "clear" is used to imply the removal of cocaine to its less addictive metabolites. Thus the cocaine esterase enzyme of the present invention has a use in therapy. Also the enzyme can be used to separate cocaine Isomers and under the correct conditions, to form cocaine analogues by the reversal of the debenzoylation reaction (biotransformation).

The following Examples illustrate the invention. "TRITON", "SEPHACEL" and "SEPHACRYL" are Registered Trade Marks.

EXAMPLE 1

Preparation of a Cocaine Esterase from the Bacterial Strain Pseudomonas maltophila MB11L Materials and Methods 1. *Pseudomonas maltophilia* (MB11L) was isolated from samples collected from a natural source by enrichment with cocaine as the sole carbon source.

MB11L was grown in 750 ml of defined medium consisting of $Na_2HPO_4$ (4.33 g), $KH_2PO_4$ (2.65 g), $NH_4Cl$ (2.0 g), $N(CH_2CO_2H)_3$ (0.1 g) per liter, containing 4 ml/l of a mineral salt solution as described by Rosenberger and Elsden (J. Gen. Microbiol. (1960) 22 726–739). Cocaine (90% pure w/w) was added aseptically as the sole carbon source (10 mM) to 750 ml of the above sterile medium in a 2 liter Ehrlenmeyer flask and shaken at 250 rev/min in a shaking incubator. For bulk preparation of bacteria, 750 ml of seed culture was asceptically added to a 10 liter culture vessel, containing 9.5 liter of sterile medium. The bulk cultures were incubated at 30° C., stirred at 500 rev/min with sterile aeration at 18 l/min. The growth medium for the bulk culture was 10 mM of said cocaine with the addition of 40 mg/l D,L-methnonine and 700 µl Antifoam A emulsion (Sigma), which is a 30% aqueous emulsion of silicone polymers.

Cell-free extracts were prepared from cells grown in the above manner. If cells were to be harvested from a 10 liter bulk culture, prior concentration of the cell broth to 2–3 liters was performed in a rotary concentrator fitted with a 200 sq cm membrane of 0.45 µm pore size. The cells were then washed with 1 liter of growth medium. These cells or those obtained directly from a smaller volume culture were then pelleted by spinning at 10,000 g for 15 min at 4° C. in a Sorvall RC-5C centrifuge fitted with a GS-3 rotor. These pelleted cells were resuspended in 2 ml of 50 mM MOPS buffer (pH7), per gram wet cell weight. Cells were disrupted by sonication in an MSE Soniprep (Fisons Instruments, FSA Ltd.) using 18×12 µm burst of 15 seconds, alternated with 30 seconds of cooling in melting ice. Cell debris and unbroken cells were removed by centrifugation at 48,000 g for 20 min at 4° C. in a Sorvall RC-5C centrifuge using a SS-34 rotor, to give clarified cell-free extract.

2. Chemicals

Cocaine free base was obtained by dissolving the hydrochloride (5 g, 15 mmoles) in a minimum volume of distilled water, followed by the dropwise addition of 1.5 ml of 10M sodium hydroxide solution. The resulting free base was extracted into 10 ml diethylether and recovered by evaporation. A typical yield was 80%, melting point 96.4°–98° C.

The resolution and identification of cocaine and its breakdown products, and benzoic acid was determined by HPLC analysis at 218 nm or 275 nm on Waters 600 system. The 0.46×25 cm column contained 5 µm Spherisorb (C-18). The mobile solvent phase was as described by Noggle & Clark (J. Assoc. Off. Anal. Chem. (1982) 65 756–761) and Masoud and Krupski (J. Anal. Toxicol. (1980) 4 305–310). The mobile phase was sparged with helium at 30 ml/min throughout operation.

3. Buffers

The following buffers were used in the purification and characterisation of cocaine esterase.

Buffer A: 50 mM MOPS, 2% glycerol (v/v), 1 mM β-mercapto-ethanol, pH 7.0.

Buffer B: 50 mM MOPS, 0.5% (w/v) cholate, 0.1M NaCl, 2% (v/v) glycerol, 1 mM β-mercaptoethanol, pH 7.0.

Buffer C: 50 mM sodium borate, 0.5% (w/v) cholate, 0.6M NaCl, 2% (w/v) glycerol, 1 mM β-mercaptoethanol, pH 9.0.

Buffer D: 10 mM $K_2HPO_4$ 0.5% (w/v) cholate, 0.1M NaCl, 2% (v/v) glycerol, 1 mM β-mercaptoethanol, pH 6.8

4. Assays

Cocaine Esterase

Cocaine esterase in extracts, column fractions and characterisation experiments (e.g. pH optimum, Michaelis constant determinations) was routinely assayed by shaking incubation (250 rpm, 30° C.) of 2 mM cocaine HCl (made up in 1 ml 50 mM MOPS buffer, pH 7.0) with a known quantity of sample (10–200 µl, 0–0.01 U) for a fixed length of time (10–30 min). The reaction was stopped by the addition of 10 µl of concentrated phosphoric acid and protein pelleted at 13,000 rpm in a minifuge. The amount of benzoic acid produced was determined by HPLC analysis of 50 µl of the supernatant and comparison to standard samples (0–1 mM) treated identically. Standard curves of peak height plotted against benzoic acid concentration were linear over the range 0–1 mM. Controls containing no enzyme solution were run to allow for background hydrolysis. An assay was considered invalid if no cocaine remained at the end of the assay (seen by HPLC). One unit of esterase activity is defined as the amount of enzyme required to produce 1 µmol of benzoic acid in 1 min at 30° C.

The presence of esterase in a sample could be detected in a similar fashion using gas chromatography to observe benzoic acid production, but no attempt to quantify the assay was made.

Gas chromatography was used in these Examples, but as previously discussed, is an impractical tool for routine portable measurement of cocaine or cocaine esterase.

All spectrophotometric assays were performed on Perkin Elmer Lambda 3, 5 or 7 Dual Beam Spectrophotometers fitted with chart recorders and constant temperature cell jackets. Readings were against appropriate blanks.

Protein

Protein was routinely assayed by the Coomassie dye-binding method of Bradford (Anal. Biochem. (1976) 72 248–254) using commercially available reagent and Bovine Serum Albumin standard (Pierce Ltd.—obtained through Life Science Labs Ltd., Luton). An aliquot (20 µl) of sample containing 0.2–1 mg protein/ml was added to 1 ml of reagent and the reaction allowed to develop for 5 min at room temperature prior to reading the absorbance at 595 nm against a blank of buffer (20 µl) plus reagent (1 ml). Comparison to a standard curve of standard values (0–1 mg/ml) allowed calculation of the protein concentration in the sample.

Gel Filtration Standards

The following enzymes were used as molecular weight markers in gel filtration experiments: Bovine liver catalase, yeast alcohol dehydrogenase and yeast C300 hexokinase (molecular weights 240,000, 150,000, 100,000 Daltons respectively). Assays for their activity were as described in Bergmeyer ((1986) Methods of Enzymatic Analysis. 3rd Edition, published by V.C.H. Publishers, Weinhelm, Germany). Cytochrome c (molecular weight 13,000 Daltons) was detected by virtue of its absorbance at 505 nm.

EXAMPLE 2

Purification of Cocaine Esterase

All steps were carried out at 4° C. unless otherwise stated.

A cell free extract of *P. maltophilia* MB11L was prepared by sonicating and clarifying in cholate-free buffer A. Cholate was subsequently added to a concentration of 0.5% (w/v). Prior to DEAE-Anion Exchange Chromatography, the pH was checked and NaCl added to give a final conductivity of 13 mS/cm. The final salt concentration typically approached 0.1M, but was carefully controlled to ensure binding to DEAE Sephacel.

1. DEAE-Sephacel Chromatography

Figure 2:
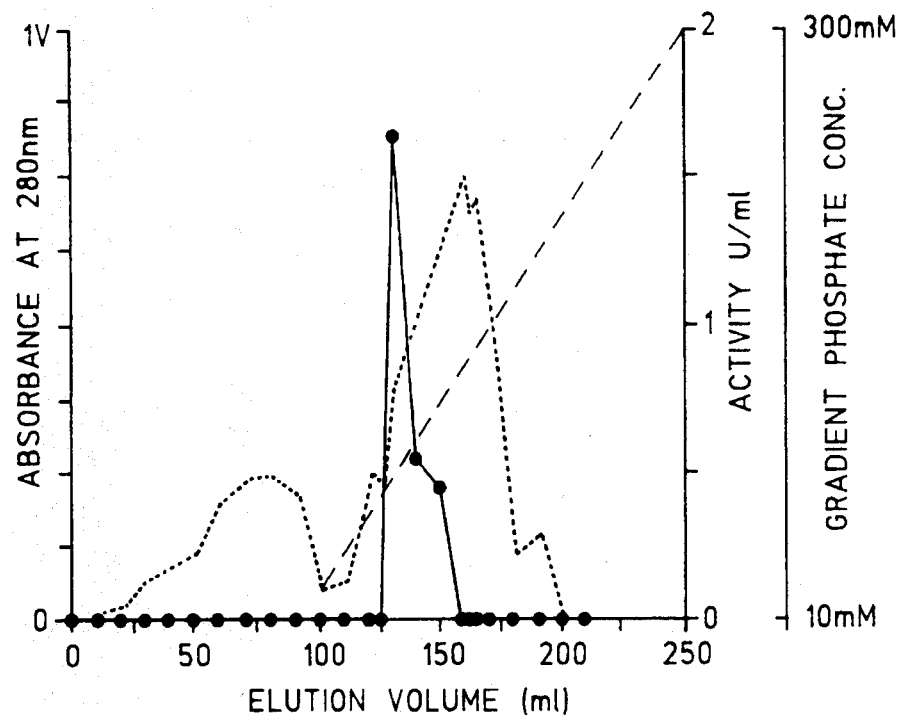

Cell free extract, typically containing 900 mg of solubilised protein was loaded on to a 27×2.6 cm DEAE-Sephacel (Pharmacia/LKB Biotechnology Ltd.) column pre-equilibrated in buffer B. Loading, washing and elution of the column was at 15 ml/sq.cm/h. After washing with buffer B until no further elution of protein was detected at 280 nm, the cocaine esterase was eluted with a combined salt and pH gradient 125 ml each of buffer B to buffer C followed by a wash of 100 ml buffer C. Eluting protein was collected as 10 ml fractions which were assayed for cocaine esterase activity and protein. (As shown in FIG. 1, the enzyme eluted at approximately 0.4M NaCl, pH 8.3. In this and each of the following figures esterase activity is denoted by filled circles and protein content by the dotted line. In FIGS. 1 and 2 the dashed line represents the elution gradient). Active fractions were pooled and dialysed against 2 liter quantities of buffer D. (The DEAE-column was routinely cleaned with 1M NaCl/1% Triton X-100 (v/v) and 0.1M NaOH prior to storage in 0.02% (w/v) azide.

2. Hydroxylapatite Chromatography

Dialysed protein (20–200 mg) was routinely loaded on to a 14×1.6 cm Bio-gel HT (Bio-Rad Laboratories Ltd.) hydroxlyapatite column. The column was pre-equilibrated in buffer D, and the protein material checked for equivalent pH (6.8) and conductivity (13 mS/cm) prior to loading. A flow rate of 15 ml/sq.cm/h was maintained throughout loading, washing and elution. After loading, the column was washed until no further eluting protein was detected at 280 nm with buffer D. Elution of the esterase was with a gradient of 30 ml each of buffer D to buffer E (identical to buffer D except that 300 mM potassium phosphate was used) followed by a wash of 30 ml of buffer E. Fractions (3 ml) were collected and assayed for cocaine esterase activity. A typical elution profile is shown in FIG. 2. Active fractions were pooled and concentrated against PEG 4000 (20% w/v) to a final volume of approximately 4 ml. (The column was routinely cleaned with 1M NaCl/0.5% (w/v) cholate and stored in 0.02% (w/v) azide).

3. AcA 44 Gel Filtration Chromatography

Figure 3:
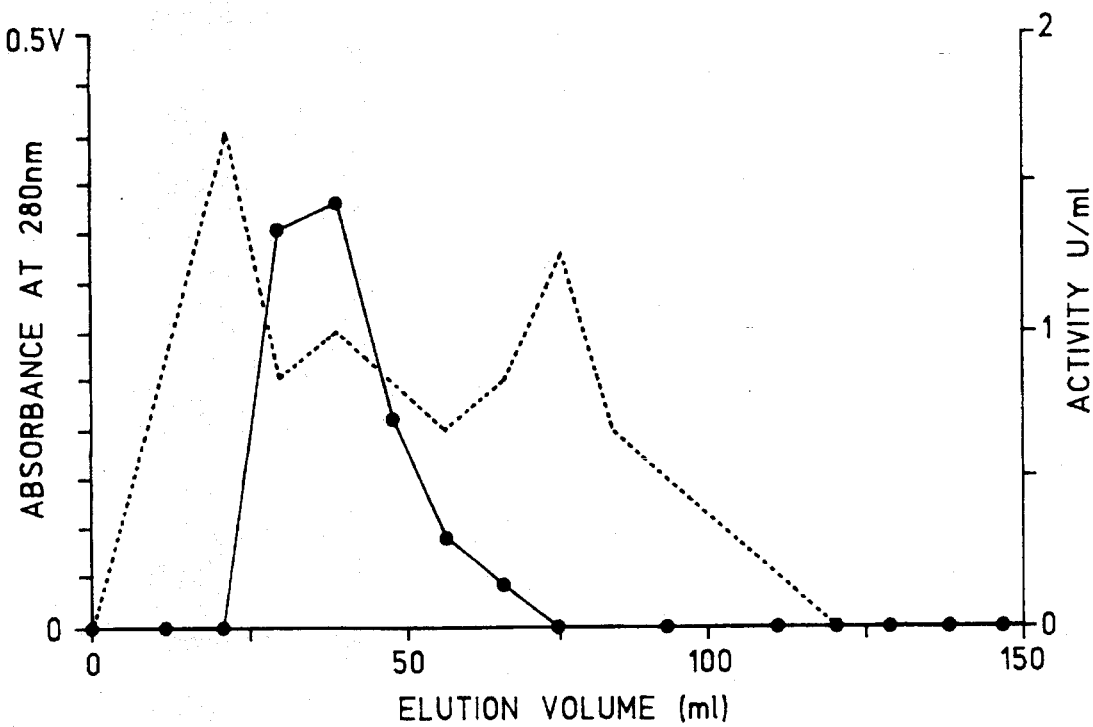

Cocaine esterase from the previous step was concentrated to approximately 4 ml and loaded on to a 60×1.6 cm column of AcA 44 Ultrogel (Life Science Laboratories Ltd.) which had been pre-equilibrated in buffer B. In the presence of cholate, the cocaine esterase would be expected to elute as a protein with a molecular weight of 110,000 Daltons. Elution with buffer B was performed at a flow rate of 4 ml/sq.cm/h and the elute collected as 2 ml fractions. Assays for cocaine esterase activity were performed. A typical elution profile is shown in FIG. 3. Active fractions were pooled for cholate removal.

4. Removal of cholate

The pooled enzyme was diluted 1:10 with buffer A (to bring the cholate concentration below the critical micelle concentration) and dialysed against 2×10 volumes of the same buffer to remove salt and cholate. Cholate removal was monitored by simply adding 20 µl of sample to 1 ml of Coomassie dye binding protein assay reagent, which contains phosphoric acid as a major component. Under the acidic conditions, cholate-containing samples formed a vivid blue precipitate due to the precipitation of cholic acid. Post-AcA 44 material treated as described above did not produce this precipitate, even after subsequent concentration, indicating effective removal of cholate.

5. Sephacryl S-300 Gel Filtration Chromatography

Figure 4:
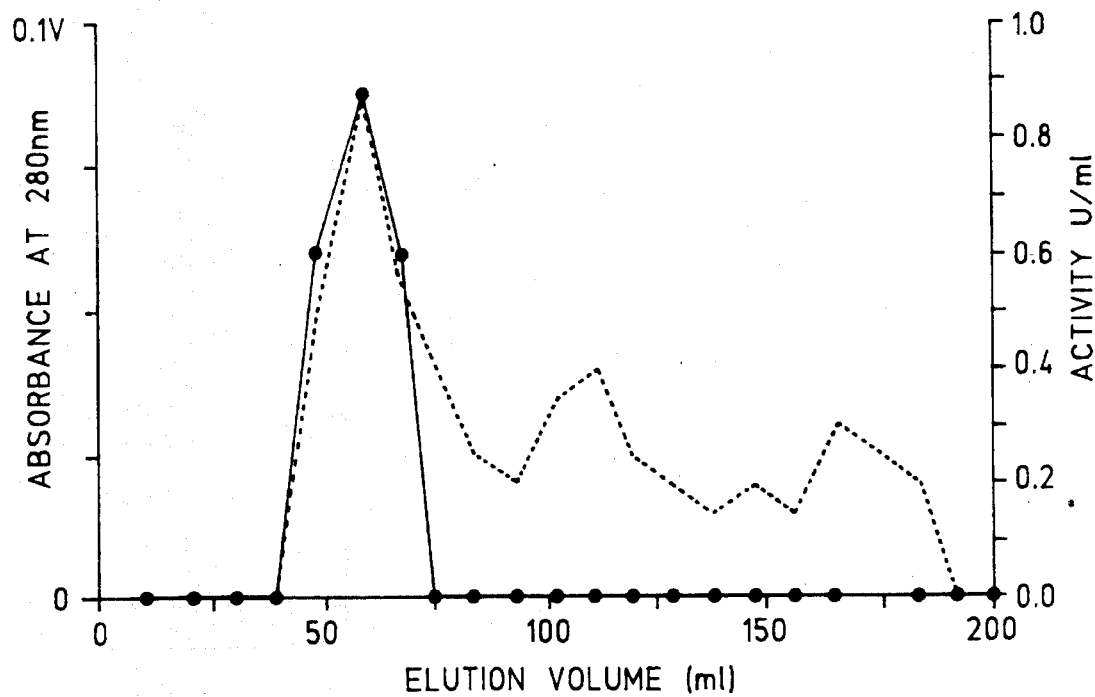

Concentrated cholate-free esterase was loaded on to a 75×1.6 cm column of Sephacryl S-300 (Pharmacia LKB Biotechnology Ltd.) pre-equilibrated in buffer A. Subsequent elution with buffer A was at a flow rate of 4 ml/sq.cm/ h. In this cholate-free state the esterase was expected to elute as a protein with molecular weight 410,000 Daltons. Collection and assay of 2 ml fractions typically gave a profile as shown in FIG. 4.

Results

In a solubilised extract of *P. maltophilia* MB11L grown on cocaine as the carbon source, cocaine esterase was present at a specific activity of 0.16 unit (mg protein)$^{-1}$. It was purified 22-fold as shown in Table 1 below.

EXAMPLE 3

Characterisation of Cocaine Esterase pH Optimum

Purified cocaine esterase material (10 µl, 5 µg protein) was incubated for 20 min at 30° C. with 2 mM cocaine in a range of buffers: 50 mM Bis Tris Propane (pH 6.0, 7.0, 8.0, 9.0 and 10.0), 50 mM MOPS (pH 6.5, 7.0 and 7.5) and 50 mM Bicine (pH 7.5, 8.5 and 9.0). After removal of protein by precipitation with 10 µl concentrated phosphoric acid and centrifugation at 13,000 rpm in a microfuge, the benzoic acid concentration in each incubation was determined by HPLC analysis and cocaine esterase activity determined. In each case a control assay was performed containing no enzyme, and the assay calibrated using a 1 mM benzoate standard. All assays were performed in duplicate.

Cocaine esterase displayed a pH optimum range from 7 to 9. Tertiary amine buffers appeared to have an inhibitory effect on the esterase activity.

Effect of Temperature

Samples of cell-free extract were held at various temperatures for at least 30 min prior to centrifugation. Assays for cocaine esterase activity and protein were compared to original levels. The enzyme was stable up to 30° C., above which enzyme activity fell off rapidly.

A comparison of the thermal stabilities of CE and acetylesterase activities in the purified protein preparation (0.015 mg protein) was performed at 47° C. in the presence and absence of cholate. The $t_{1/2}$ of acetyl esterase was 4.5 min in the presence of cholate and approximately 10 min in its absence. CE had a $t_{1/2}$ of 2.5 min in the presence of cholate and little instability in its absence.

Kinetic Characterisation and Substrate Specificity of Cocaine Esterase

Incubations of purified cocaine esterase (1.25 µg of protein) were performed in 1 ml of 50 mM bis-tris-propane buffer, pH 8.0, with substrates over the concentration range 0–2 mM (0–1 mM for cocaine) at 30° C. for 10 min. Reactions were stopped using concentrated phosphoric acid (10 µl) to precipitate protein, which was removed by centrifugation at 13,000 rpm in a Microfuge. Rates of substrate hydrolysis were calculated from HPLC analyses of the incubations. Non-enzymic rates of hydrolysis were calculated from control samples containing no enzyme, and the enzyme assays corrected accordingly. Standard samples of the relevant free acids were used to calibrate each assay. From the results it was possible to calculate apparent $K_m$ and $V_{max}$ values for cocaine esterase against each substrate. Lineweaver-Burke and Eadie-Hofstee plots were used to obtain these values (see Fersht, 1985, Enzyme Structure and Mechanism, 2nd Edition, Publishers: W. H. Freeman & Co., Oxford for methods). The mean values are listed in Table 2.

TABLE 2

| SUBSTRATE | Apparent $K_m$ (mM) | Apparent $V_{max}$ (U/mg) |
| --- | --- | --- |
| Cocaine | 0.36 | 29.5 |
| Ethyl benzoate | 1.89 | 65.0 |
| Ethyl 2-hydroxycenzoate | 1.75 | Not determined |
| Ethyl 3-hydroxybenzoate | No activity | No activity |
| Ethyl 4-hydroxybenzoate | No activity | No activity |

Thus, Michaelis constants obtained using the purified enzyme show that cocaine esterase has a greater affinity for cocaine than ethyl benzoates, but hydrolyses cocaine at a slower rate than ethyl benzoates.

Molecular Weight Determination

The molecular weight of the native/solubilised enzyme was determined by the method of Andrews (Blochem. J. (1964) 91 222–233). For the solubilised enzyme, measurements were performed on a column of Sephacryl S-200 (1.6×75 cm). Purified cocaine esterase (2 mg protein) was solubilised and mixed with marker proteins and the mixture (total volume 2 ml) added to the column. The column was eluted with buffer B at 4 ml/cm$^2$/h collecting as 1.3 ml fractions. The elution volume of cocaine esterase corresponded to a molecular weight of 110,000 Daltons. The molecular weight of the aggregated cocaine esterase was performed in a similar manner on a Sephacryl S-300 column, but no solubilisation was performed and elutton was with buffer A. The elution volume of cocaine esterase corresponded to a molecular weight of 410,000 Daltons.

Molecular weight determination was also performed using SDS-PAGE. The purified cocaine esterase sample ran as a distinct major band corresponding to a molecular weight of 129,000 Daltons when compared to standard proteins

TABLE 1

| Purification Step | Total volume (ml) | Total activity (U) | Overall recovery % | Total protein (mg) | Specific activity (U/mg) | Overall purification (fold) |
| --- | --- | --- | --- | --- | --- | --- |
| Solubilised extract | 150 | 163 | 100 | 1017 | 0.16 | 1.0 |
| DEAE-Sephacel Anion exchange Chromatography | 120 | 98 | 60 | 141 | 0.70 | 4.4 |
| Hydroxylapatite HT | 64 | 57 | 35 | 57 | 1.0 | 6.3 |
| AcA 44 Ultrogel Gel filtration | 28 | 46 | 28 | 20 | 2.30 | 14 |
| S-300 Sephacryl Gel filtration | 23 | 14 | 9 | 4 | 3.50 | 22 | using the method of Shapiro et al. (Biochem. Biophys. Res. Comms. (1967) 28 815–820). This similar value to that of the solubilised enzyme implies that any effect of detergent/protein interactions in determining the molecular weight of the solubilised enzyme were minimal.

Native PAGE analysis of purified CE showed a major band of Rf 0.2, the gel was sectioned using a scalpel blade, and incubations containing sections of the gel with 2 mM cocaine In buffer were analysed for cocaine esterase activity. HPLC analysis of the incubations confirmed that the region of the gel corresponding to the Rf 0.2 major band, hydrolysed cocaine at a rate higher than the other regions of the gel sampled.

Inhibition Studies

Samples of purified cocaine esterase (0.01 U) were incubated with a range of possible inhibitors (1 mM) at 30° C. for 10 min prior to assaying for activity against cocaine in the usual manner. The possible inhibitors tested were phenylmethylsulphonyl fluoride (PMSF), eserine, para-hydroxymercuribenzoate (pHMB), benzoate and ecgonine methyl ester. Cocaine esterase activity was determined in a control sample containing no Inhibitor. The results in Table 3 below show that PMSF causes total inactivation of cocaine esterase activity, whilst the other possible active site inhibitors, eserine and pHMB were relatively ineffective as inhibitors.

TABLE 3

| INHIBITOR | % ACTIVITY RELATIVE TO CONTROL |
|---|---|
| 1 mM PMSF | 0 |
| 1 mM Eserine | 95 |
| 1 mM pHMB | 86 |
| 1 mM Benzoate | 92 |

TABLE 3-continued

| INHIBITOR | % ACTIVITY RELATIVE TO CONTROL |
|---|---|
| 1 mM Ecgonine methyl ester | 82 |

Activities are relative to that determined with 2 mM cocaine in the absence of inhibitor (0.9 U/ml=100% activity).

Activities of Commercial Esterases Against Cocaine

A number of commercially available esterase enzymes were screened for their ability to hydrolyse cocaine to benzoic acid and ecgonine methyl ester by incubation with cocaine (2 mM) under conditions reported as optimal for their usual activity by the manufacturer. Hydrolysis of cocaine was monitored by HPLC and the results are listed in Table 4. Control incubations containing no enzyme were performed under each set of conditions to allow accurate assaying of enzyme activity. As none of the enzymes tested showed appreciable activity compared to that shown against their usual substrate, the cocaine esterase from MB11L, appears unique in its ability to attack the benzoate ester linkage of cocaine.

TABLE 4

Screen of esterases for activity against cocaine
Esterase activity with cocaine was monitored by HPLC as described earlier. Reaction mixtures contained 2 mM cocaine in 50 mM buffer of pH suited for maximum enzyme activity in each case. The activities of the enzymes against cocaine are compared to their usual substrates in the table below.

| ENZYME | SPECIFIC ACTIVITY (U/mg) AGAINST COCAINE | SPECIFIC ACTIVITY (U/mg) AGAINST USUAL SUBSTRATE |
|---|---|---|
| Porcine pancreatic lipase | 0 | 50 |
| Orange peel acetylesterase | 0 | 6.2 |
| Porcine liver esterase | 0.833 | 20 |
| Horse serum butyrylcholinesterase | 0.098 | 14 |
| α-chymotrypsin (with calcium) | 0.04 | 40 |
| Electric eel acetylcholinesterase | 0 | 320 |
| Cocaine esterase[1] | 3.5 | — |
| Atropinesterase[2] | 0 | 1.5[3] |

[1]Purified enzyme from MB11L.
[2]A sample of crude extract from *Psuedomonas putida* PMBL-1 grown on atropine as sole carbon source with 0.05 U of atropine hydrolysing activity (measured by HPLC) was incubated with 2 mM cocaine for 20 min at 30° C. No breakdown of cocaine was seen by HPLC analysis.
[3]This value is from crude extract studies by Stevens ((1969) PhD Thesis, University of Leiden, Netherlands). Purified atropinesterase has a specific activity of 500–600 U/mg (Hessing, (1983), PhD Thesis, University of Leiden, Netherlands).

Effect of Growth Substrate on Cocaine Esterase Activity

MB11L cells were grown in 750 ml batch culture on a range of carbon sources (10 mM) in medium B. After 3 sub-inoculations cells were harvested and crude extracts prepared. Assays for cocaine esterase and protein were performed and the results expressed relative to levels seen in extracts from the cells grown on cocaine (0.02 µmol/min/mg protein=100%), are shown in Table 5.

TABLE 5

| ENZYME | RELATIVE ENZYME ACTIVITY GROWTH SUBSTRATE | | | |
| --- | --- | --- | --- | --- |
|  | Benzoate | Citrate | Cocaine | Glucose |
| Cocaine esterase | 20% | 0% | 100% | 20% |

These results clearly demonstrate the low levels of cocaine esterase from cells grown in the absence of cocaine (cells grown on benzoate or glucose give extracts possessing only 20% of the specific activity of cells grown on cocaine, whilst citrate grown cells possess no activity), indicating that cocaine esterase is inducible. Inclusion of 40 mg/l D,L-methionine in the growth medium increased the specific activity of the cocaine esterase produced by 20%.

We claim:

1. An isolated cocaine esterase obtainable from Pseudomonas sp NCIMB 40427 or a mutant thereof having the following properties:

(1) it catalyses the debenzoylation of cocaine;

(2) it has a molecular weight in the unaggregated form of about 120,000 Daltons as determined by gel filtration;

(3) it has esterase activity specifically at the benzoate ester linkage of cocaine, (4) it separates at a major band of Rf about 0.2 on PAGE, in its aggregated form; and (5) it is completely inhibited by 1 mM phenylmethylsulphonyl fluoride but ineffectively inhibited by 1 mM eserine, each determined at 30° C. with respect to 2 mM cocaine as substrate.

2. A process of producing the cocaine esterase of claim 1 which comprises culturing Pseudomonas sp NCIMB 40427 or a mutant thereof capable of producing the cocaine esterase, together with a source of carbon and nitrogen, at a temperature of 20° to 40° C., disrupting the cells and recovering the cocaine esterase from the disrupted cells.

3. A method of detecting cocaine in a sample, comprising adding the cocaine esterase of the sample to claim 1 to debenzoylation of cocaine in the sample to produce ecgonine methyl ester and benzoic acid, and detecting the occurrence of said debenzoylation.

4. A method according to claim 3 wherein benzoate ions of the benzoic acid liberated in the debenzoylation are detected.

5. A method according to claim 4 wherein the benzoate ions are detected conductimetrically.

* * * * *